United States Patent [19]

Fedorov et al.

[11] Patent Number: 4,615,700
[45] Date of Patent: Oct. 7, 1986

[54] ARTIFICIAL EYE LENS

[75] Inventors: Svyatoslav N. Fedorov; Valery D. Zakharov; Alexandr O. Axenov, all of Moscow, U.S.S.R.

[73] Assignee: Moskovsky Nauchno-Issledovatelsky Institut Mikrokhirurgii Glaza, Moscow, U.S.S.R.

[21] Appl. No.: 649,981

[22] Filed: Sep. 13, 1984

[51] Int. Cl.⁴ .............................................. A61F 2/16
[52] U.S. Cl. ........................................................ 623/6
[58] Field of Search .................................. 3/13; 623/6

[56] References Cited

U.S. PATENT DOCUMENTS 4,366,582 1/1983 Faulkner ..................................... 3/13

FOREIGN PATENT DOCUMENTS 1103399 5/1955 France ....................................... 3/13

OTHER PUBLICATIONS

"Nuevos Modelos de Lentes Plasticas de Camara Anterior" by Barraquer, Joaquin, *Anales del Instituto Barraquer*, Sep. 1961, pp. 345-352.

"Lens Styles from Cilco (advertisement brochure), Cilco, Inc., 1616 13th Ave., Box 1680, Huntington, West Va. 25717, pp. 1, 5 and 6, Stein Posterior Chamber Lens Style SN-1 on p. 5 relied upon, Oct. 1982.

*Primary Examiner*—Ronald L. Frinks
*Attorney, Agent, or Firm*—Fleit, Jacobson, Cohn & Price

[57] ABSTRACT

An artificial eye lens, in which there is a lens body and three elastic supporting elements fixed on the lens body. Two supporting elements are shaped as rods, while one element is shaped as an angle-piece. The rod-shaped elements are arranged on the side diametrically opposite to the angle-piece. The aforesaid two rod-like elements make an angle 45 to 90 degrees with the plane passing through the vertex of the angle-piece and through the center of the lens body. All the supporting elements are so bent out as to lie parallel to the principal optical plane of the lens body.

2 Claims, 2 Drawing Figures

ARTIFICIAL EYE LENS

FIELD OF THE INVENTION

The present invention relates generally to medicine, and more specifically to ophthalmology and has particular reference to an artificial eye lens (or lenticulus) adapted to use as prosthetophakia or prosthetic eye lens in treatment, e.g., a cataract.

BACKGROUND OF THE INVENTION

It is common knowledge that surgical treatment of various eye diseases frequently necessitates the removal of the eye crystalline lens (lensectomy) followed by substituting the eye lens with an artificial intraocular lens or lenticulus. As a rule, the majority of such artificial eye lenses need further suturing of the supporting elements to the iris, which is in fact a rather complicated surgical intervention, especially when the the lens is to be fixed to the inferior portion of the iris. This operation is fraught with possible dislocation of the lens when the pupil is being dilated, such being the case if the lens is introduced through a puncture in the iris which is known, e.g., from USSR Inventor's Certificate No. 545.352, wherein an artificial lens provides for the presence of a lens and supporting legs outside the pupillary area, and the lens has at least one loop-shaped leg to pass a suture attaching the lens to the iris.

With a view to attaining a simplified artificial lens implantation technique and its more reliable fixing, another artificial eye lens has been devised as described in USSR Inventor's Certificate No. 858.819. In such an artificial lens the top loop-shaped leg is in effect composed of two lugs arranged opposite to each other in a horizontal plane of the lens in its top portion, and the plane of said loop-shaped leg is offered at an angle 5 to 8 degrees with the plane of the lens so as to establish springiness. A bottom supporting leg is also provided.

A disadvantage inherent in the aforesaid known artificial lens resides in the fact that it involves the formation of a large incision (up to 4 mm long) in the top portion of the iris, followed by application of a Supramid suture, which prolongs substantially the operative time and offers additional difficulties during the lens implantation procedure. Moreover, a possibility cannot be ruled out for the pupil deformation and enlargement of the iridotomy as a result of the suture cutting through thinned spherical changed structures resulting from a prolonged compression of the iridal tissues. This in turn may lead not only to dislodging but also to off-centring of the artifial eye lens. In addition, such an artificial eye lens may frequently be the cause of an inflammatory reaction of the eye due to forceful interaction of the lens supporting elements with the eye tissues rich in blood vessels and nerves.

SUMMARY OF THE INVENTION

It is an object of the present invention to provide an artificial eye lens that would be in fact less traumatic to the adjacent tissues than those known in the art, due to a lower weight thereof.

It is another object of the present invention to simplify the artificial lens implantation techniques and to reduce an incision made for the purpose.

These and other objectives are attained due to the fact that in an artificial eye lens, comprising a lens body and three elastic supporting elements secured on the lens, two of which elements are located on the side diametrically opposite to the third element made as an angle-piece. According to the invention two elements situated on the same diametral side of the lens body are shaped as rods arranged symmetrically with respect to the plane passing through the vertex of said angle-piece and making an angle 45 to 90 degrees with the plane. All the supporting elements are bent out so as to lie parallel to the principal optical plane of the lens body.

It is expedient that the rod has a length corresponding to the distance from the point of its attachment to the lens body, to the corresponding point of attachment of the angle-piece supporting element to the lens.

The artificial eye lens proposed herein is implanted into the posterior eye chamber so that all its supporting elements, that is, the angle-piece and two rods, are situated in the plane parallel to the plane of the posterior surface of the capsule on which the lens is to be fixed, thereby preventing a possibility for the lens supporting elements to contact the eye tissues rich in blood vessels and nerve twigs. This means that the lens supporting elements cause no inflammatory reaction in the eye. Such a positioning of the proposed lens in the posterior eye chamber, more precisely, on the crystalline capsule or on its remainder portion (in the case of a traumatic cataract), contributes to retention of the diaphragmal functions of the pupil and makes it possible, whenever necessary, to dilate the pupil medicinally without any risk of dislocation of the lens itself or of its supporting elements. The proposed lens construction provides for soft and easy implantation thereof. Two rod-shaped supporting elements can be so compressed at the instant of implanting as to be within the limits of the lens, whereby the incision for the lens introduction can be as long as the size of the lens proper which results in reduced traumatization of the eye tissues, diminished possible bleeding and less pronounced postoperative astigmatism, since the longer the operative incision the greater number of blood vessels and nerve branches are affected and the more pronounced is astigmatism.

And, last but not least, simple construction of the supporting elements makes it possible to greatly reduce the lens weight, which tells considerably on its interaction with the adjacent tissues, since the lens exerts less pressure upon the tissues and the amplitude of its oscillations during movements of the eyeball is reduced.

BRIEF DESCRIPTION OF THE DRAWINGS

In what follows the invention will be illustrated by the description of a specific exemplary embodiment thereof to be read in conjunction with the accompanying drawings, wherein.

DESCRIPTION OF PREFERABLE EMBODIMENT OF THE INVENTION

Figure 1:
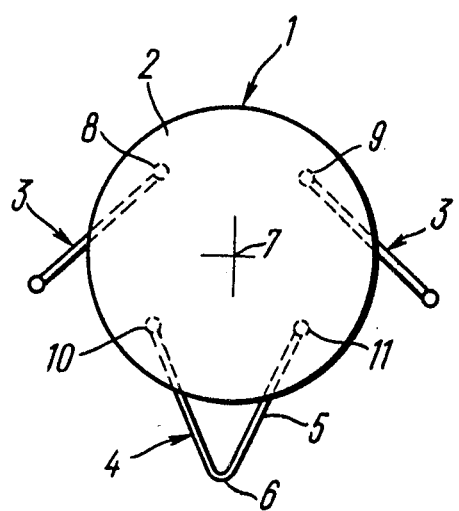
FIG. 1 is a diagrammatic front view of an artificial eye lens, according to the invention.

Now referring to FIG. 1 showing the artificial eye lens indicated as a whole under Ref. No. 1, which comprises a lens 2 proper of any heretofore-known construction, e.g., a biconvex lens as can be best seen from FIG. 2, two supporting elements 3 shaped as rods, and a supporting element 4 shaped as an angle-piece.

The rod-shaped supporting elements 3 may be made of any material featuring high elasticity, e.g., Supramid (proprietary name). The rods are fixed with one of its ends in the bulk of the lens 2 outside the field of vision of the lens (as shown with a dash-and-dot line in the Figure), while their vacant ends project beyond the lens limits.

The supporting element 4 shaped as an angle-piece, is fixed with its both legs 5 in the bulk of the lens 2 so that its vertex 6 is located in the plane passing through a centre 7 of the lens. The element 4 may be made of any elastic material, e.g., Supramid.

As it can be seen from FIG. 1, points 8 and 9 of attachment of the rods 3 and points 10 and 11 of attachment of the angle-piece 4, are arranged pairwise, that is, the points 8 and 10, and the points 9 and 11, on imaginary straight lines parallel to each other and to the plane passing through the vertex of the angle-piece and through the centre of the lens. Thus, the points 8, 9, 10, 11 are spaced equally apart from the edges of the lens 2 in a direction square with the line passing through the vertex of the angle-piece and through the centre of the lens. The rods should be inclined towards the angle-piece at an angle 45 to 90 degrees to the plane (the angle being equal to 45 degrees in the embodiment of FIG. 1). The length of the rods is selected preferably so as to be substantially equal to the distance between the points 8, 9, 10, and 11. The reason for it will be more obvious hereinbelow on consideration of the implantation techniques of the proposed lens. The supporting elements 3 are arranged symmetrically with respect to the plane passing through the vertex 6 of the angle-piece and through the centre 7 of the lens.

Figure 2:
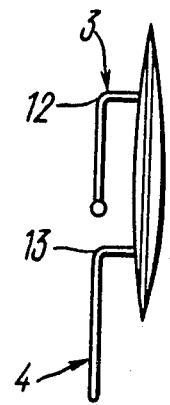
FIG. 2 is a side view of the lens of FIG. 1.

It is obvious from FIG. 2 that both the supporting elements 3 and the angle-piece 4 are bent out so as to form a square bend or elbow, respectively at 12 and 13 and are arranged largely parallel to the principal plane of the lens. It should be noted that the above said elbow is not necessarily a square one, and all the supporting elements of the lens should be arranged substantially in the same plane in order to attain the maximum stability of the lens after implantation.

Now let us consider the implantation techniques of the aforedescribed lens.

A corneoscleral incision 3 to 4 mm long is performed under local anesthesia to form a conjunctival flap 2 to 3 mm wide. The pupil is made to dilate with a one-percent lysaton administered to the anterior eye chamber. A membranous cataract or the posterior crystalline capsule (in the case of aphakia) is dissected by a cystotome, a 2.5 to 3 mm long incision being made along the 6 to 12 o'clock meridian.

The artificial lens is implanted with the aid of a tenaculum forceps, taking hold of the artificial lens in such a manner that the supporting elements 3 shaped as two rods, should catch the grooves in the tenaculum forceps and are so pressed with their vacant ends against the lens 2 as to approach closely to the attachment points of the supporting element 4 shaped as an angle-piece. As a result, the supporting element 4 occurs to be in advance as along the direction of the lens introduction pathway. Then the effective portion of the forceps carrying the artificial lens is brought into the anterior eye chamber so that the supporting element 4 made as an angle-piece should pass through the incision into the crystalline capsule of the secondary membranous cataract and should arrange behind the capsule. Next the forceps is opened and brought out of the eye chamber, with the result that both of the rod-shaped supporting elements get straightened and occur in the same plane with the angle-shaped element behind the crystalline capsule. Thereupon the pupil is made to contract with an acetylcholine solution administered into the anterior eye chamber, and the wound is hermetically stitched by applying 3 or 4 Nylon 10-0 intermittent sutures. An antibiotic solution is administered under the conjunctiva for the purpose of prophylaxis, ristomycin (20 thousand AU) in an amount of 3 ml being used for the purpose.

EXAMPLE 1

Male patient K., aged 32 was admitted to the Eye Department on Apr. 14, 1981, the diagnosis being one of the secondary membranous semiresolved stationary traumatic cataract on the right eye, the left eye being in sound conditions.

On admission:
OD=0.02, not amenable to correction
OS=1.0

On Apr. 15, 1981 a surgery for discision of the membranous cataract, followed by implantation of an artificial eye lens +23,OD in the right eye. Both the operation and the postoperative period uneventful.

At dismissal: Vis
OD—0.9
OS—I.0
Three months later
OD—0.9
Six months later
OD—0.9.

EXAMPLE 2

Female patient K., aged 24 was admitted to the Eye Department on Apr. 25, 1981 with the diagnosis of the secondary membranous traumatic cataract on the right eye, the left eye being normal.

On admission:
OS=1.0
OD=0.01, is not amenable to correction.

On Apr. 26, 1981 a surgery for discision of the membranous cataract, followed by implantation of an artificial eye lens +22.0 in the right eye.

Both the operation and the postoperative period uneventful. A first degree postoperative inflammatory reaction occurred.

At dismissal: Vis—OD—0.8 to 0.9, not amenable to correction.

What we claim is:

1. An artificial eye lens, comprising:
   a lens body;
   three supporting elements, a first, second and third, made of an elastic material and fixed on said lens body, two of said elements, the first and second, being located on the side diametrically opposite to said third element, said third element being shaped like an angle-piece fixed with its lens in said lens body, while said first and second elements situated on the same diametrical side, are rods with one end fixed in said lens body and arranged symmetrically with respect to the plane passing through the vertex of said angle-piece and through the centre of said lens body and making an angle 45 to 90 degrees with said plane, all the aforesaid elements, said first, second and third being bent out to form an elbow so that said elements are located parallel to the principal optical plane of said lens body.
2. An artificial eye lens as claimed in claim 1, wherein each of said rods has a length corresponding to the distance between the point of attachment to said lens body and the corresponding point of attachment of said angle-piece to said lens body.

* * * * *